(12) United States Patent
Nolan

(10) Patent No.: US 7,109,348 B1
(45) Date of Patent: Sep. 19, 2006

(54) SYNTHESIS OF 1,3 DISTRIBUTED IMIDAZOLIUM SALTS

(75) Inventor: Steven P. Nolan, New Orleans, LA (US)

(73) Assignee: University of New Orleans Research and Technology Foundation, Inc., New Orleans, LA (US)

( * ) Notice: Subject to any disclaimer, the term of this patent is extended or adjusted under 35 U.S.C. 154(b) by 83 days.

(21) Appl. No.: 10/653,688

(22) Filed: Sep. 2, 2003

Related U.S. Application Data

(60) Provisional application No. 60/407,073, filed on Aug. 30, 2002.

(51) Int. Cl.
*C07D 233/54* (2006.01)
(52) U.S. Cl. .................. 548/335.1; 548/300.1
(58) Field of Classification Search ............. 548/335.1, 548/300.1
See application file for complete search history.

(56) References Cited

U.S. PATENT DOCUMENTS

| 5,077,414 A | 12/1991 | Arduengo, III |
| 5,182,405 A | 1/1993 | Arduengo, III |
| 6,316,380 B1 | 11/2001 | Nolan et al. |

OTHER PUBLICATIONS

Arduengo et al., Tetrahedron, 1999, 55:14523-14534.*
Jafarpour et al., J. of Organometallic Chemistry, 2000, 606:49-54.*

* cited by examiner

*Primary Examiner*—Kamal A. Saeed
*Assistant Examiner*—Robert Shiao
(74) *Attorney, Agent, or Firm*—Garvey, Smith, Nehrbass & North, L.L.C.; Seth M. Nehrbass

(57) ABSTRACT

Imidazolium salts are the immediate precursors to N-heterocyclic carbenes (NHC) yet a simple, general synthetic route to a wide variety of imidazolium salts is not yet available. Such a straightforward route is described for two specific members of this family of ligand precursor: 1,3-Bis (2,4,6-trimethylphenyl)imidazolium chloride (IMes.HCl) and 1,3-Bis(2,6-diisopropylphenyl)imidazolium chloride (IPr.HCl). The procedure appears general and similar protocols can be used to isolate various imidazolium salts.

17 Claims, No Drawings

SYNTHESIS OF 1,3 DISTRIBUTED IMIDAZOLIUM SALTS

CROSS-REFERENCE TO RELATED APPLICATIONS

Priority of U.S. Provisional Patent Application Ser. No. 60/407,073, filed 30 Aug. 2002, incorporated herein by reference, is hereby claimed.

STATEMENT REGARDING FEDERALLY SPONSOREED RESEARCH OR DEVELOPMENT

This material is based upon work supported by the National Science Foundation (Contract No. 9985213).

Any opinions, findings, and conclusions or recommendations expressed in this material are those of the inventors and do not necessarily reflect the views of the National Science Foundation.

REFERENCE TO A "MICROFICHE APPENDIX"

Not applicable.

BACKGROUND OF THE INVENTION

1. Field of the Invention

The present invention relates to imidazolium salts. More particularly, the present invention relates to methods of producing imidazolium salts.

2. General Background of the Invention

N-heterocyclic carbenes[1], so called "phosphine-mimics", have attracted considerable attention as possible alternatives for the widely used phosphine[2] ligands in homogeneous catalysis.[3,4]

Diagram A:

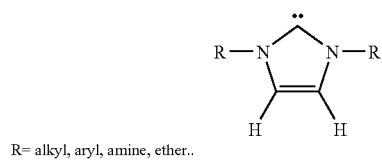

R= alkyl, aryl, amine, ether..

The primary advantage of these ligands appears to be that they do not easily dissociate from the metal center, and as a result an excess of the ligand is not required in order to prevent aggregation of the catalyst usually affording the bulk metal[5]. The use of these ligands in palladium-catalyzed Heck[6], Suzuki-Miyaura[7], Stille[8], Sonogashira[9], aryl amination[10], telomerization of butadiene[11], Hiyama[12], Kumada-Corriu reactions[13,14,15], rhodium-assisted hydrosilylation[16], iridium-mediated olefin hydrogenation[17] and ruthenium-mediated olefin metathesis[7,8] has opened new opportunities in catalysis. The synthesis of the NHC generally involves the deprotonation of the imidazolium precursor by action of a base.

Diagram B:

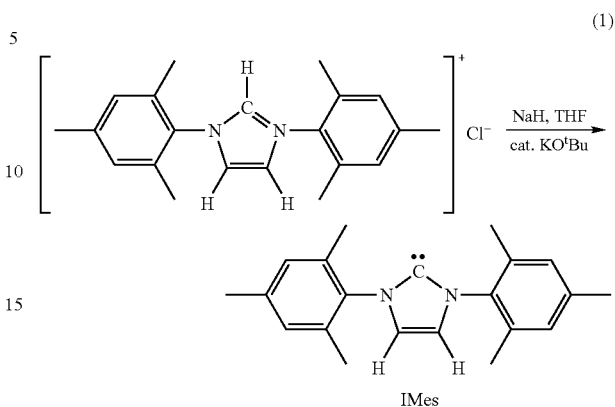

The synthesis of the imidazolium salts as reported by Arduengo[18] involves a condensation reaction with concomitant azeotropic removal of water at elevated temperatures.

Diagram B:

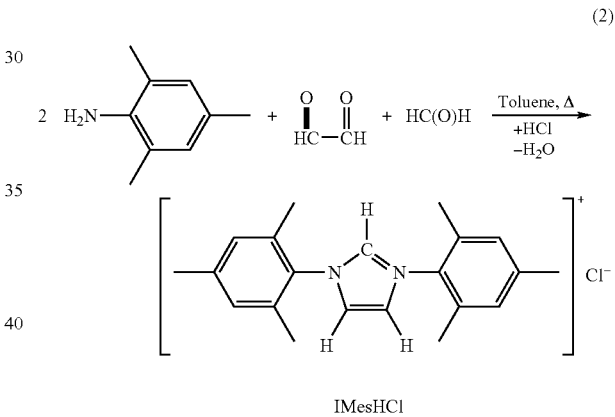

This protocol is not general for aryl bearing imidazolium and sterically congested imidazolium salts (bulky groups on nitrogen) often fails or leads to low yields of product.

The previously reported synthetic procedures for the preparation of imidazolium salts necessitated high temperature, dry solvents and handling under inert atmosphere.[18] An alternative method employed molecular sieves to absorb the water generated in the condensation reaction. It also required heating for long reaction times.[2] It should also be noted that these reaction times would have to be significantly longer if these protocols were performed on very large scale. As a result of prolonged heating, decomposition occurs and tars are generated which render product isolation difficult and isolated yield lower than optimum. As some imidazolium salts are not at all amenable to assembly using the "one-pot" protocol, we have explored the possibility of performing the condensation reactions in a two-step procedure.

The following U.S. patents are incorporated herein by reference: U.S. Pat. Nos. 5,077,414; 5,182,405; and 6,316,380

BRIEF SUMMARY OF THE INVENTION

The present invention comprises a method of synthesizing imidazolium in high purity.

Imidazolium salts IMes.HCl (2) and IPr.HCl (4) are efficient supporting ligands in metal-catalyzed reactions (see above) and it is with these two targets in mind that an assembly protocol was tested. Since the condensation in one pot led to only decomposition or side-product in the formation of the sterically congested IPr.HCl (4), we reasoned that the assembly probably involved more than one step and that obviously under these reaction conditions other reaction pathways were accessible in view of presumably slow kinetics associated with bulky substituents. We tested this hypothesis by first synthesizing the diimine compounds, 1 and 3. Indeed the diimine bearing the bulky 2,6 diisopropylaryl group 3 does form rather slowly. These diimine can then be subjected to ring closure conditions (paraformaldehyde and HCl) at or below room temperature in various solvents. The addition of paraformaldehyde and HCl in dioxane is routinely carried out at 0° C. but can be done at room temperature without deleterious effect on yield and purity. The improved syntheses of imidazolium salts presented are conducted in air and make use of readily available solvents such as methanol and ethylacetate without a need for solvent pre-drying steps. A variety of salts can be formed including those with various counterions. The counterion can be selected by judicious choice of acid (e.g., $HPF_6$ for $PF_6$ counterion)

Diagram D:

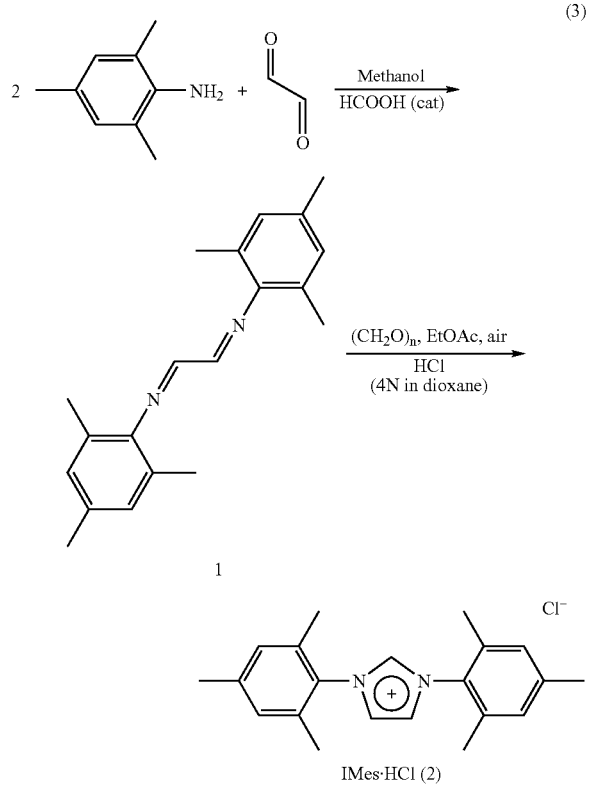

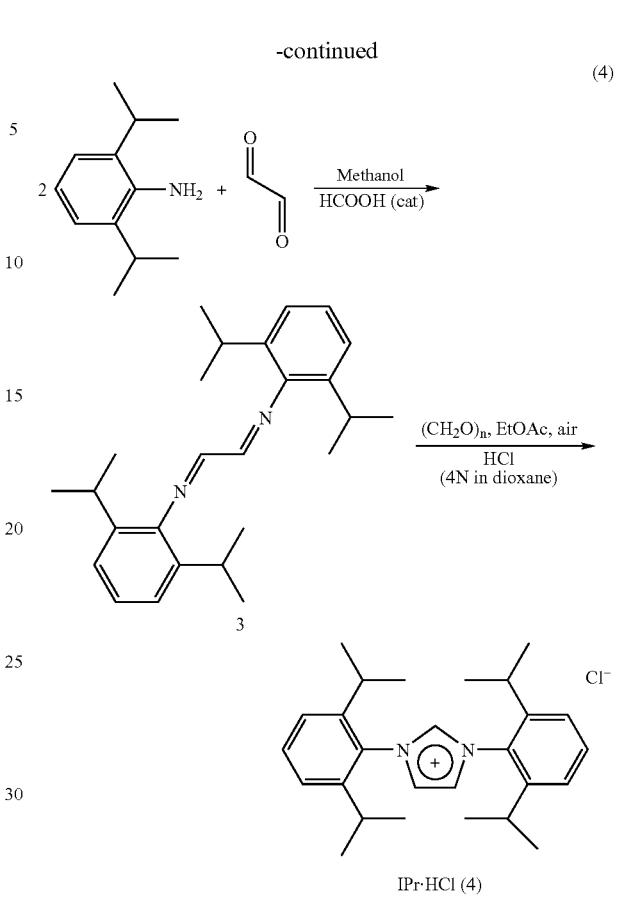

A high yield, two-step synthetic protocol has been developed leading to imidazolium salts in a straightforward manner. This procedure has significant advantages over existing methodologies as the two reactions used in the imidazolium assembly involve room temperature reactions and two filtrations that can both be carried out in air. This two-step approach is to date the unique route to 4.

The present invention includes a method of preparing an imidazolium salt comprising providing (as by synthesizing) a diimine compound and subjecting the diimine compound to ring closure conditions. The diimine compound is preferably from the group consisting of 1,3, diaryldiazabutadiene, 1,3, dialkyldiazabutadiene, and 1,3, arylalkyldiazabutadiene; and paraformaldehyde and a protic acid (such as HCl, $HBF_4$, or $HPF_6$, and preferably HCl) preferably provide the ring closure conditions. The diimine compound can be 1, in which case the salt is 2; the diimine compound can be 3, in which case the salt is 4 (4 is also an embodiment of the present invention); the diimine compound can be 1,3, arylalkyldiazabutadiene (in which case the salt produced is also an embodiment of the present invention). Preferably, the diimine compound is subjected to ring closure conditions at or below room temperature. The salt preferably includes a counterion, and the counterion is determined by the acid used for ring closure. The diimine compound can be synthesized at room temperature.

Preferably, the diimine compound is mixed with a solvent from the group consisting of methanol, ethyl acetate (most preferably), ethanol, tetrahydrofuran, and toluene before being subjected to ring closure. Preferably, the synthesis of the diimine compound and the ring closure are carried out in air. Preferably, no solvent pre-drying steps are performed.

The present invention includes the imidazolium salt 1,3-Bis(2,6-diisopropylphenyl)imidazolium chloride.

The present invention includes a method of preparing an imidazolium salt comprising providing a diimine compound from the group consisting of 1 and 3, mixing the diimine compound with a solvent from the group consisting of: methanol, ethyl acetate, ethanol, tetrahydrofuran, and toluene; and at or below room temperature, mixing the diimine compound and solvent with paraformaldehyde and a protic acid. When the diimine compound is 1, the salt is 2; when the diimine compound is 3, the salt is 4.

DETAILED DESCPITION OF THE INVENTION

The present invention comprises a two-step method of preparing imidazolium salts comprising:

Carrying out all reactions in air unless otherwise indicated.

Synthesizing of 1,3-Bis(2,4,6-trimethylphenyl)imidazolium chloride (IMes.HCl, 2) by Charging a 1 L round bottom flask with methanol (500 mL), 2,4,6-trimethylaniline (97 mL, 689 mmol), glyoxal (40 wt % solution in water, 38.8 mL, 313.5 mmol), and formic acid (1 mL).

Stirring the resulting mixture for 3 hours at room temperature.

Filtering the yellow precipitate formed, (1) Diagram D.

Washing precipitate with cold methanol.

Drying precipitate in vacuo overnight (91.0%, 74.5 g, 313.5 mmol).

Charging a 5 L round bottom flask with 1 (100 g, 342 mmol) and ethyl acetate (2000 mL).

Cooling solution to 0° C.

Charging a 500 mL Erlenmeyer flask with paraformaldehyde (13.35 g, 445 mmol) and HCl (4N in dioxane, 136.9 mL, 548 mmol,).

Stirring this solution for 10 minutes then add it to the cooled solution of 1.

Stirring the reaction mixture for a total reaction time of 2.5 hours.

Collecting the beige precipitate formed by filtration.

Drying the precipitate.

Dissolving precipitate in 100 ml of dichloromethane.

Adding Sodium bicarbonate (10.0 g) to the solution.

Stirring the mixture for 1 hour or until the solution stopped bubbling.

Filtering the solution to remove the solids.

Precipitating the product with 100 ml of diethyl ether

Collecting product by filtration

Washing product with ether

Drying product in vacuo to yield IMes.HCl (2) as an off-white powder (66%, 77.1 g, 226 mmol). $^1$H NMR (CDCl$_3$, 400 MHz) δ 11.02 (s, 1H), 7.58 (s, 2H), 7.04 (s, 4H), 2.32 (s, 6H), 2.2 (s, 12H); $^{13}$C NMR (CDCl$_3$, 400 MHz) δ 141, 139, 134, 130.5, 129.8, 124, 21, 17.8.

Synthesizing of 1,3-Bis(2,6-diisopropylphenyl)imidazolium chloride (IPr.HCl, 4) by Charging a 1000 mL round bottom flask with methanol (500 mL), 2,6-diisopropylaniline (63.8 mL, 340 mmol), glyoxal (40 wt % soln in water, 19 mL, 170 mmol), and formic acid (1 mL).

Stirring the resulting mixture for 3 hours at room temperature.

Filtering the yellow precipitate, (3) (Diagram D)

Washing precipitate with cold methanol.

Drying precipitate in vacuo overnight (70%, 44.2 g, 238 mmol).

Charging a 5 L round bottom flask with precipitate (3) (200 g, 532 mmol) and ethyl acetate (2 L).

Stirring the resulting mixture until (3) was dissolved.

Cooling the solution to 0° C. but this can be carried out at room temperature.

Charging a 500 mL Erlenmeyer flask with paraformaldehyde (20.7 g, 690 mmol), HCl (4N in dioxane, 212 mL, 851 mmol).

Stirring this solution for 10 minutes, then added.

Stirring the resulting mixture for 2 hours at room temperature.

Filtering precipitate

Dissolving precipitate in methanol (200 mL).

Adding 15.0 g of sodium bicarbonate.

Stirring the solution for 1 hour or until there is no more carbonation.

Filtering the solution to remove the solids.

Reprecipitating the product with 250 mL of diethyl ether

Collecting product by filtration

Washing product with diethyl ether.

Drying the product in vacuo to yield IPr.HCl (4) as a white powder (70%, 158.25 g, 371 mmol). $^1$H NMR (CDCl$_3$, 400 MHz) δ 10.1 (s, 1H), 8.15 (s, 2H), 7.57 (t, 2H, J=7.8 Hz), 7.35 (d, 4H, J=8.4 Hz), 2.43(m, 4H), 1.28 (m, 24H) $^{13}$C NMR (CDCl$_3$, 400 MHz) δ 145, 132.1, 129.9, 126.8, 124.7, 29.1, 24.7, 23.7.

EXAMPLE 1

General Considerations. $^1$H and $^{13}$C nuclear magnetic resonance spectra were recorded on a Varian-300 or Varian-400 MHz spectrometer at ambient temperature in CDCl$_3$ (Cambridge Isotope Laboratories, Inc.). All reactions were carried out in air unless otherwise indicated.

Synthesis of 1,3-Bis(2,4,6-trimethylphenyl)imidazolium chloride (IMes.HCl, 2)

A 1 L round bottom flask was charged with methanol (500 mL), 2,4,6-trimethylaniline (97 mL, 689 mmol), glyoxal (40 wt % solution in water, 38.8 mL, 313.5 mmol), and formic acid (1 mL). The resulting mixture was allowed to stir for 3 hours at room temperature. The yellow precipitate (1) formed was filtered, washed with cold methanol and dried in vacuo overnight (91.0%, 74.5 g, 313.5 mmol). A 5 L round bottom flask was charged with 1 (100 g, 342 mmol) and ethyl acetate (2000 mL). The solution was cooled to 0° C. A 500 mL Erlenmeyer flask was charged with paraformaldehyde (13.35 g, 445 mmol) and HCl (4N in dioxane, 136.9 mL, 548 mmol,). This solution was stirred for 10 minutes then added. The reaction mixture was stirred for a total reaction time of 2.5 hours. The beige precipitate formed was collected by filtration, dried and dissolved in 100 ml of dichloromethane. Sodium bicarbonate (10.0 g) was added to the solution and the mixture was stirred for 1 hour or until the solution stopped bubbling. The solution was then filtered to remove the solids and the product was precipitated with 100 ml of diethyl ether, collected by filtration, washed with ether, and dried in vacuo to yield IMes.HCl (2) as an off-white powder (66%, 77.1 g, 226 mmol). $^1$H NMR (CDCl$_3$, 400 MHz) δ 11.02 (s, 1H), 7.58 (s, 2H), 7.04 (s, 4H), 2.32 (s, 6H), 2.2 (s, 12H); $^{13}$C NMR (CDCl$_3$, 400 MHz) δ 141, 139, 134, 130.5, 129.8, 124, 21, 17.8.

Synthesis of
1,3-Bis(2,6-diisopropylphenyl)imidazolium chloride
(IPr.HCl, 4)

A 1000 mL round bottom flask was charged with methanol (500 mL), 2,6-diisopropylaniline (63.8 mL, 340 mmol), glyoxal (40 wt % soln in water, 19 mL, 170 mmol), and formic acid (1 mL). The resulting mixture was allowed to stir for 3 hours at room temperature. The yellow precipitate (3) was filtered, washed with cold methanol and dried in vacuo overnight (70%, 44.2 g, 238 mmol). A 5 L round bottom flask was charged with 3 (200 g, 532 mmol) and ethyl acetate (2 L) and the resulting mixture was stirred until 3 was dissolved. The solution was cooled to 0° C. A 500 mL Erlenmeyer flask was charged with paraformaldehyde (20.7 g, 690 mmol), HCl (4N in dioxane, 212 mL, 851 mmol). This solution was stirred for 10 minutes, then added. The resulting mixture was then stirred for 2 hours at room temperature. The precipitate was filtered, dissolved in methanol (200 mL) and 15.0 g of sodium bicarbonate was added. The solution was stirred for 1 hour or until there was no more carbonation. The solution was filtered to remove the solids and the product was reprecipitated with 250 mL of diethyl ether, collected by filtration, washed with diethyl ether and dried in vacuo to yield IPr.HCl (4) as a white powder (70%, 158.25 g, 371 mmol). $^1$H NMR (CDCl$_3$, 400 MHz) δ 10.1 (s, 1H), 8.15 (s, 2H), 7.57 (t, 2H, J=7.8 Hz), 7.35 (d, 4H, J=8.4 Hz), 2.43(m, 4H), 1.28 (m, 24H) $^{13}$C NMR (CDCl$_3$, 400 MHz) δ 145, 132.1, 129.9, 126.8, 124.7, 29.1, 24.7, 23.7.

More information about the present invention can be found in the paper attached to U.S. Provisional Patent Application Ser. No. 60/407,073 and entitled: "Synthesis of 1,3 Disubstituted Imidazolium Salts" by Roy A. Kelly, William Sommer and Steven P. Nolan.

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

REFERENCES (a) Regitz, M. *Angew. Chem. Int. Ed. Engl.*, 1996, 35, 725–728.
(b) Arduengo, A. J. III; Krafczyk, R. *Chem. Zeit.* 1998,32, 6–14.
(c) Herrmann, W. A.; Köcher, C. *Angew. Chem. Int. Ed. Engl.*, 1997,36,2163–2187.
Applications of phosphine ligands in homogeneous catalysis:
(a)Collman, J. P.; Hegedus, L. S.; Norton, J. R.; Finke, R. G. "Principles and Applications of Organotransition Metal Chemistry"; University Science Books, Mill Valley, CA, 1987.
(b)Parshall, G. W.; Ittel, S. "Homogeneous Catalysis" J. Wiley and Sons, New York. 1992.
(c)Pignolet, L. H., Ed. "Homogeneous Catalysis with Metal Phosphine Complexes", Plenum: New York, 1983.
(a) Weskamp, T.; Schattenmann, W. C.; Spiegler, M.; Herrmann, W. A. *Angew. Chem. Int. Ed. Engl.* 1998, 37, 2490–2493.
(b) Scholl, M.; Trnka, T. M.; Morgan, J. T.; Grubbs, R. H. *Tetrahedron Lett.* 1999, 40, 2247–2250.
(a) Huang, J.; Stevens, E. D.; Nolan, S. P.; Petersen, J. L. *J. Am. Chem. Soc.* 1999, 121, 2674–2678.
(b) Huang, J.; Schanz, H.-J.; Stevens, E. D.; Nolan, S. P. *Organometallics,* 1999, 18, 2370–2375.
Voges, M. H.; Rømming, C.; Tilset, M. *Organometallics,* 1999, 18, 529–533.
(a)Yang, C.; Lee, H. M.; Nolan, S. P. *Org. Let.* 2001, 3, 1511–1514.
(b)Yang, C.; Nolan, S. P. *Synlett.* 2001, 1539–1542.
(a)Zhang, C.; Huang, J.; Trudell, M. T.; Nolan, S. P. *J. Org. Chem.* 1999, 64, 3804–3805.
(b) Grasa, G. A.; Viciu, M. S.; Huang, J.; Zhang, C.; Trudell, M. L.; Nolan, S. P. *Organometallics,* 2002, 21, 2866–2873.
Grasa, G. A.; Nolan, S. P. *Org. Let.* 2001, 3, 119–122.
Yang, C.; Nolan, S. P. *Organometallics,* 2002, 20, 1020–1022.
(a)Huang, J.; Grasa, G.; Nolan, S. P. *Org. Lett.* 1999, 1, 1307–1309.
(b) Grasa, G. A.; Viciu, M. S.; Huang, J.; Nolan, S. P. *J. Org. Chem.* 2001, 66, 7729–7737.
Jackstell, R.; Andreu, M.; Frisch, A.; Selvakumar, K.; Zapf, A.; Klein, H.; Spannenberg, A.;
Röttger, D.; Briel, O.; Karch, R.; Beller, M. *Angew. Chem. Int. Ed.* 2002, 41, 986–989.
Lee, H. M.; Nolan, S. P. *Org. Lett.* 2000, 2, 2053–2055.
Huang, J.; Nolan, S. P. *J. Am. Chem. Soc.* 1999, 121, 9889–9890.
Herrmann, W. A.; Reisinger, C.-P.; Spiegler, M. *J. Organomet. Chem.* 1998, 557, 93–96.
(a) Herrmann, W. A.; Elison, M.; Fisher, J.; Köcher, C.; Autus, G. R. J. *Angew. Chem. Int. Ed. Engl.,* 1995, 34, 2371–2373.
(b) Herrmann, W. A.; Fischer, J.; Elison, M.; Köcher, C.; Autus, G. R. J. *Chem. Eur. J.* 1996, 2, 772–780.
(c) McGuinness, D. S.; Green, M. J.; Cavell, K. J.; Skelton, B. W.; White, A. H. J. *Organomet. Chem.* 1998, 565, 165–178.
Herrmann, W. A.; Goossen, L. T.; Köcher, C.; Autus, G. R. J. *Angew. Chem. Int. Ed Eng.* 1996, 35, 2805–2807.
(a)Lee, H. M.; Jiang, T.; Stevens, E. D.; Nolan, S. P. *Organometallics,* 2001, 20, 1255–1258.
(b) Hillier, A. C.; Lee, H. M.; Stevens, E. D.; Nolan, S. P. *Organometallics,* 2001, 20, 4246–4252.
(a) Arduengo, A. J. III. U.S. Pat. No. 5,077,414, 1991.
(b) Arduengo, A. J. III.; Krafcyk, R.; Schmutzler, R. *Tetrahedron* 1999, 55, 14523–14534.

What is claimed is:

1. A method of preparing an imidazolium salt comprising:
(a) synthesizing a diimine compound; and
(b) subjecting the diimine compound to ring closure conditions at or below room temperature, wherein:
paraformaldehyde and a protic acid provide the ring closure conditions.

2. The method of claim 1, wherein:
the diimine compound is from the group consisting of 1,3, diaryldiazabutadiene, 1,3, dialkyldiazabutadiene, and 1,3, arylalkyldiazabutadiene.

3. The method of claim 1, wherein the diimine compound is

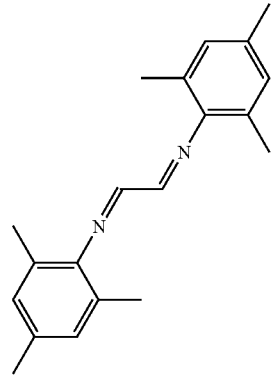

4. The method of claim 1, wherein the diimine compound is

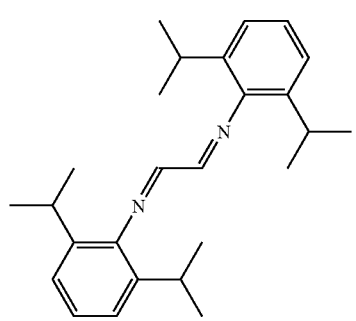

5. The method of claim 1, wherein the salt includes a counterion.

6. The method of claim 5, wherein the counterion is determined by the acid used for ring closure.

7. The method of claim 1, wherein the diimine compound is synthesized at room temperature.

8. The method of claim 1, wherein between steps (a) and (b) the diimine compound is mixed with a solvent from the group consisting of: methanol, ethyl acetate, ethanol, tetrahydrofuran, and toluene.

9. The method of claim 1, wherein the synthesis of the diimine compound and the ring closure are carried out in air.

10. The method of claim 1, wherein no solvent pre-drying steps are performed.

11. The salt prepared by the method of claim 2 when the diimine compound is 1,3, arylalkyldiazabutadiene.

12. The invention of claim 1, wherein the protic acid is HCl, HBF$_4$, or HPF$_6$.

13. The invention of claim 1, wherein the protic acid is HCl.

14. The method of claim 8, wherein the solvent is ethyl acetate.

15. A method of preparing an imidazolium salt comprising:
   (a) providing a diimine compound from the group consisting of

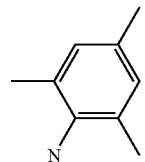

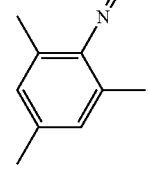

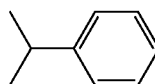 and

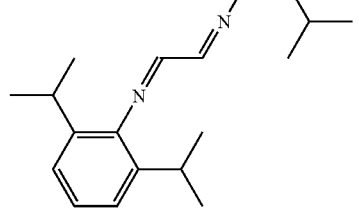 ;

(b) mixing the diimine compound with a solvent from the group consisting of: methanol, ethyl acetate, ethanol, tetrahydrofuran, and toluene; and (c) at or below room temperature, mixing the diimine compound and solvent with paraformaldehyde and a protic acid.

16. The method of claim 15, wherein the diimine compound is

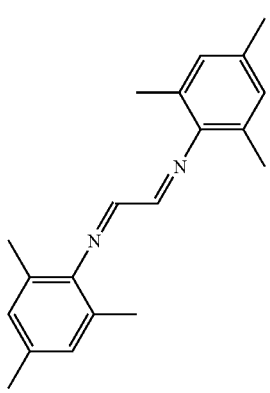

and the imidazolium salt is

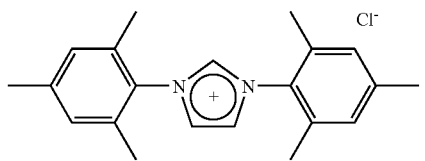

17. The method of claim 15, wherein the diimine compound is
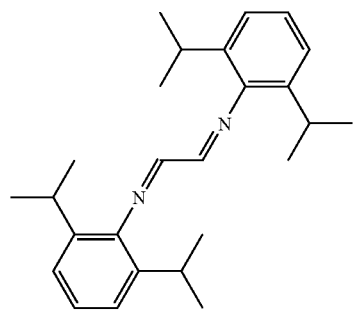
and the imidazolium salt is
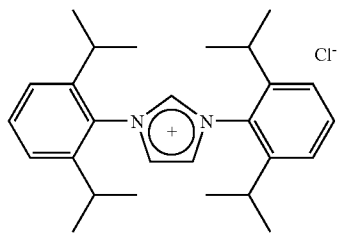
* * * * *